United States Patent
Alarifi (10) Patent No.: US 11,547,567 B2
(45) Date of Patent: Jan. 10, 2023

(54) ARTIFICIAL BONE STRUCTURE AND METHOD OF MANUFACTURING ARTIFICIAL BONE STRUCTURE

(71) Applicant: Majmaah University, Al-Majmaah (SA)

(72) Inventor: Ibrahim M. Alarifi, Riyadh (SA)

(73) Assignee: Majmaah University, Al-Majmaah (SA)

( * ) Notice: Subject to any disclaimer, the term of this patent is extended or adjusted under 35 U.S.C. 154(b) by 0 days.

(21) Appl. No.: 17/134,718

(22) Filed: Dec. 28, 2020

(65) Prior Publication Data

US 2022/0202572 A1    Jun. 30, 2022

(51) Int. Cl.
    *A61F 2/30* (2006.01)
    *A61F 2/44* (2006.01)
    *A61F 2/28* (2006.01)

(52) U.S. Cl.
    CPC ............. *A61F 2/28* (2013.01); *A61F 2/3094* (2013.01); *A61F 2002/30143* (2013.01); *A61F 2002/30235* (2013.01); *A61F 2002/30948* (2013.01); *A61F 2002/30985* (2013.01); *A61F 2310/00293* (2013.01)

(58) Field of Classification Search
    None
    See application file for complete search history.

(56) References Cited

U.S. PATENT DOCUMENTS

| | | | | |
|---|---|---|---|---|
| 4,863,474 A | * | 9/1989 | Brown | A61F 2/30907 623/23.54 |
| 5,496,372 A | * | 3/1996 | Hamamoto | A61F 2/44 606/907 |
| 5,679,299 A | * | 10/1997 | Gilbert | A61L 24/0094 156/185 |
| 5,807,406 A | * | 9/1998 | Brauker | B01D 69/02 433/201.1 |
| 6,863,694 B1 | * | 3/2005 | Boyce | A61B 17/8085 623/23.61 |
| 6,905,516 B1 | * | 6/2005 | Lemaitre | A61F 2/28 623/23.62 |

(Continued)

FOREIGN PATENT DOCUMENTS

CN    110169846 A  *  8/2019  ............... A61F 2/28

*Primary Examiner* — Ann Schillinger
(74) *Attorney, Agent, or Firm* — Perilla Knox & Hildebrandt LLP; Kenneth A. Knox (57) ABSTRACT

Disclosed is an artificial bone structure for replacement of natural bone and comprising a solid cylindrical portion having an elongate shape. The solid cylindrical portion comprises an auxetic structure of a plurality of artificial osteons and each artificial osteon comprises a first hexagonal unit and a second hexagonal unit having corresponding edges. Furthermore, a first artificial osteon and a second artificial osteon of the plurality of artificial osteons are connected to each other using an edge of a third artificial osteon and about a central axis of each of the first artificial osteon and the second artificial osteon. Moreover, the artificial bone structure comprises a hollow cylindrical portion having an elongate shape, disposed inside of and concentrically with the solid cylindrical portion. The hollow cylindrical portion is configured to comprise an artificial bone marrow therein.

6 Claims, 3 Drawing Sheets

(56) References Cited

U.S. PATENT DOCUMENTS

| | | | | |
|---|---|---|---|---|
| 8,287,915 B2* | 10/2012 | Clineff | ................. | A61L 27/46 |
| | | | | 424/602 |
| 2005/0112397 A1* | 5/2005 | Rolfe | ................. | A61F 2/4455 |
| | | | | 606/76 |
| 2007/0116734 A1* | 5/2007 | Akash | ................. | A61F 2/30 |
| | | | | 264/44 |
| 2008/0077248 A1* | 3/2008 | Murillo | ................. | A61F 2/44 |
| | | | | 623/17.16 |
| 2010/0121463 A1* | 5/2010 | Tormala | ................. | A61L 27/58 |
| | | | | 623/23.75 |
| 2010/0168856 A1* | 7/2010 | Long | ................. | A61F 2/30756 |
| | | | | 623/14.12 |
| 2010/0198353 A1* | 8/2010 | Pope | ................. | C04B 35/645 |
| | | | | 623/18.11 |
| 2011/0172798 A1* | 7/2011 | Staiger | ................. | A61L 27/56 |
| | | | | 700/98 |
| 2012/0215310 A1* | 8/2012 | Sharp | ................. | B33Y 70/10 |
| | | | | 29/428 |
| 2013/0211533 A1* | 8/2013 | Fonte | ................. | A61F 2/30767 |
| | | | | 623/22.4 |
| 2019/0099273 A1* | 4/2019 | Servidio | ................. | A61F 2/0811 |
| 2021/0228360 A1* | 7/2021 | Hunt | ................. | A61F 2/38 |

\* cited by examiner

ARTIFICIAL BONE STRUCTURE AND METHOD OF MANUFACTURING ARTIFICIAL BONE STRUCTURE

TECHNICAL FIELD

The present disclosure relates generally to medical implants and more specifically, to artificial bone structures for replacement of natural bone. Furthermore, the present disclosure relates to methods of

BACKGROUND

Generally, medical implants have been used for replacement of natural body tissues in a person having suffered from damage thereof. For example, a person having suffered from an accident leading to damage of an arm bone may have to undergo a surgery to get the damaged arm bone replaced with a corresponding medical implant. Such a medical implant is required to be fabricated using a biocompatible material, such that medical implant can be accepted by body of the person as though naturally belonging as a part of the body. Correspondingly, conventional medical implants have improved biocompatibility associated therewith owing to advancement in medical science. However, limited advancement has been made to improve various properties, such as tensile strength and/or elasticity of the medical implants, to enable the properties to correspond to properties of corresponding natural tissues.

In one contemplated solution, provided is an implant including a first disc portion shaped and sized generally to correspond to a first intervertebral disc section having a pivot point positioned relative to a first surface opposite a second surface of the first disc portion and a lattice structure with a negative Poisson's ratio; a second disc portion being shaped and sized generally to correspond to a second intervertebral disc section having a pivot point receptacle positioned relative to a third surface opposite a forth surface of the second disc portion and a lattice structure with a negative Poisson's ratio where the first disc portion and the second disc portion are configured to exhibit an auxetic behavior when subject to compression generally perpendicular to a surface plane of the first surface and the second surface.

In another contemplated solution, provided is an intervertebral disc replacement includes a first layer having a lower surface for contacting a first vertebral bone, a second layer coupled to the first layer, the second layer comprising a plurality of compressible column springs, and a third layer coupled to the second layer, the third layer having an upper surface for contacting a second vertebral bone. Each of the plurality of compressible column springs comprises a plurality of stacked coils, and each of the plurality of stacked coils has a spring constant (K). At least one of the plurality of compressible column springs includes a first coil having a first spring constant and a second coil comprising a second spring constant, wherein the first spring constant is different from the second spring constant.

However, none of the aforementioned contemplated solutions provide an implant that has properties similar to natural properties of corresponding natural tissues that are to be replaced using the implant.

Therefore, in light of the foregoing discussion, there exists a need to overcome various problems associated with conventional medical implants.

SUMMARY

This section provides a general summary of the disclosure, and is not a comprehensive disclosure of its full scope or all of its features.

The present disclosure seeks to provide an artificial bone structure for replacement of natural bone. Furthermore, the present disclosure seeks to provide a method of manufacturing an artificial bone structure for replacement of natural bone.

According to an aspect, an embodiment of the present disclosure provides an artificial bone structure for replacement of natural bone, the artificial bone structure comprising:

a solid cylindrical portion having an elongate shape, wherein the solid cylindrical portion comprises an auxetic structure of a plurality of artificial osteons and wherein each artificial osteon comprises a first hexagonal unit and a second hexagonal unit having corresponding edges, wherein:
the edges of each of the first hexagonal unit and the second hexagonal unit are disposed respectively to form an open end having a predefined gap;
the predefined gap between the edges forming the open end of the first hexagonal unit is equal to the predefined gap between the edges forming the open end of the second hexagonal unit; and
the first hexagonal unit and the second hexagonal unit are disposed symmetrically about a central axis by connecting the corresponding edges of the first hexagonal unit and the second hexagonal unit having the gap to form each artificial osteon having a concave shape;
and wherein a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon; and
a hollow cylindrical portion having an elongate shape, disposed inside of and concentrically with the solid cylindrical portion, wherein the hollow cylindrical portion is configured to comprise an artificial bone marrow therein.

Optionally, each artificial osteon comprises:
an elongate length between respective top edge of the first hexagonal unit and the second hexagonal unit of each artificial osteon in a range of 5.0 to 6.5 millimeters;
the predefined gap of each of the first hexagonal unit and the second hexagonal unit in a range of 0.2 to 1.0 millimeter;
the edge of each of the first hexagonal unit and the second hexagonal unit having a length in a range of 2.5 to 3.5 millimeters; and
an angle between adjacent edges of each of the first hexagonal unit and the second hexagonal unit in a range of 60° to 75°.

Optionally, the auxetic structure of the plurality of artificial osteons comprises a gap between the first artificial osteon and the third artificial osteon in a range of 0.2 to 1 millimeter.

Optionally, a diameter of the hollow cylindrical portion is in a range of 20 to 30 millimeters and a diameter of the solid cylindrical portion is in a range of 40 to 50 millimeters.

Optionally, a length of the artificial bone structure is in a range of 50 to 70 millimeters.

Optionally, the solid cylindrical portion is fabricated using a solution of 80 to 90% by weight of hydroxyapatite and 20 to 10% respectively by weight of Polyacrylonitrile (PAN) or Dimethylformamide (DMF).

According to another aspect, an embodiment of the present disclosure provides a method of manufacturing an artificial bone structure for replacement of natural bone, the method comprising:

receiving a three-dimensional (3D) model of the natural bone;

using the 3D model of the natural bone to print a corresponding artificial bone structure using a 3D printer, wherein the artificial bone structure comprises:

a solid cylindrical portion having an elongate shape, wherein the solid cylindrical portion comprises an auxetic structure of a plurality of artificial osteons and wherein each artificial osteon comprises a first hexagonal unit and a second hexagonal unit having corresponding edges, wherein:

the edges of each of the first hexagonal unit and the second hexagonal unit are disposed respectively to form an open end having a predefined gap;

the predefined gap between the edges forming the open end of the first hexagonal unit is equal to the predefined gap between the edges forming the open end of the second hexagonal unit; and the first hexagonal unit and the second hexagonal unit are disposed symmetrically about a central axis by connecting the corresponding edges of the first hexagonal unit and the second hexagonal unit having the gap to form each artificial osteon having a concave shape;

and wherein a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon; and a hollow cylindrical portion having an elongate shape, disposed inside of and concentrically with the solid cylindrical portion, wherein the hollow cylindrical portion is configured to comprise an artificial bone marrow therein.

Optionally, the method further comprises preparing at least one filament wire for use in the 3D printer.

Optionally, each filament wire has a diameter in a range of 1 millimeter to 2 millimeters.

Optionally, each filament wire is prepared by using a solution of 80 to 90% by weight of hydroxyapatite and 20 to 10% respectively by weight of Polyacrylonitrile (PAN) or Dimethylformamide (DMF).

Optionally, the method further comprises:
stirring the solution of hydroxyapatite and PAN or DMF until the solution is homogenized; and
extruding the homogenous solution to obtain the at least one filament wire.

Optionally, the solution of hydroxyapatite and PAN or DMF is heated using to hot plate to a temperature within a range of 70° C. to 80° C.

Optionally, the method further comprises:
receiving a radiographic scan of the natural bone; and
generating the 3D model of the natural bone using the radiographic scan of the natural bone.

Optionally, a diameter of the hollow cylindrical portion is in a range of 20 to 30 millimeters and a diameter of the solid cylindrical portion is in a range of 40 to 50 millimeters.

Optionally, a length of the artificial bone structure is in a range of 50 to 70 millimeters.

Further areas of applicability will become apparent from the description provided herein. It will be appreciated that features of the present disclosure are susceptible to being combined in various combinations without departing from the scope of the present disclosure as defined by the appended claims. The description and specific examples in this summary are intended for purposes of illustration only and are not intended to limit the scope of the present disclosure.

DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

Exemplary embodiments will now be described more fully with reference to the accompanying drawings.

The exemplary embodiments are provided so that this disclosure will be thorough, and will fully convey the scope to persons skilled in the art. Numerous specific details are set forth such as examples of specific components, devices, and methods, to provide a thorough understanding of embodiments of the present disclosure. It will be appreciated by persons skilled in the art that specific details need not be employed. Exemplary embodiments may be embodied in many different forms. Thus, neither should be construed to limit the scope of the disclosure. In some example embodiments, well-known processes, well-known device structures, and well-known technologies are not described in detail.

The terminology used herein is for the purpose of describing particular exemplary embodiments only and is not intended to be limiting. As used herein, singular forms such as "a," "an," and "the" may be intended to include corresponding plural forms as well, unless the context clearly indicates otherwise. Furthermore, terms akin to "comprises," "comprising," "including," and "having," are inclusive and therefore, specify the presence of stated features, integers, steps, operations, elements, and/or components, but do not preclude the presence or addition of one or more other features, integers, steps, operations, elements, components, and/or groups thereof.

When an element or layer is referred to as being "on," "engaged to," "connected to," or "coupled to" another element or layer, it may be disposed directly on, engaged, connected or coupled to the other element or layer, or intervening elements or layers may be present therein. However, when an element is referred to as being "directly on," "directly engaged to," "directly connected to," or "directly coupled to" another element or layer, there may be no intervening elements or layers present. Other words used to describe a relationship between elements should be interpreted in a like manner (e.g., "between" versus "directly between," "adjacent" versus "directly adjacent," etc.). As used herein, the term "and/or" includes any and all combinations of one or more of the associated listed items.

Spatially relative terms such as "inner," "outer," "beneath," "below," "lower," "above," "upper," and the like may be used herein for ease of description, to describe an element's or a feature's relationship to another element(s) or feature(s) as illustrated in the figures. Furthermore, spatially relative terms may be intended to encompass different orientations of the device in use or in operation, in addition to one or more orientations depicted in the figures. For example, if the device in the figures is turned over, elements described as "below" or "beneath" other elements or features would then be oriented "above" the other elements or features. Thus, the example term "below" can encompass both an orientation of above and below. It will be appreciated that the device may be otherwise oriented (rotated 90 degrees or at other orientations) and the spatially relative descriptors used herein should be interpreted accordingly.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The term "user" or "person" relates to at least one individual that uses or operates the system or arrangement or device (or other variants thereof) as claimed, such as, by interacting with at least one component of the system or arrangement or device (or other variants thereof).

Moreover, if any method steps, processes, and operations are described, they are not to be construed as necessarily requiring their performance in the particular order discussed or illustrated, unless specifically identified as an order of performance. It is also to be understood that additional or alternative steps may be employed.

In overview, embodiments of the present disclosure are concerned with artificial bone structures for replacement of natural bone. Furthermore, embodiments of the present disclosure are concerned with methods of manufacturing artificial bone structures for replacement of natural bone.

According to an aspect, an embodiment of the present disclosure provides an artificial bone structure for replacement of natural bone, the artificial bone structure comprising:

a solid cylindrical portion having an elongate shape, wherein the solid cylindrical portion comprises an auxetic structure of a plurality of artificial osteons and wherein each artificial osteon comprises a first hexagonal unit and a second hexagonal unit having corresponding edges, wherein:

the edges of each of the first hexagonal unit and the second hexagonal unit are disposed respectively to form an open end having a predefined gap;

the predefined gap between the edges forming the open end of the first hexagonal unit is equal to the predefined gap between the edges forming the open end of the second hexagonal unit; and the first hexagonal unit and the second hexagonal unit are disposed symmetrically about a central axis by connecting the corresponding edges of the first hexagonal unit and the second hexagonal unit having the gap to form each artificial osteon having a concave shape;

and wherein a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon; and a hollow cylindrical portion having an elongate shape, disposed inside of and concentrically with the solid cylindrical portion, wherein the hollow cylindrical portion is configured to comprise an artificial bone marrow therein.

According to another aspect, an embodiment of the present disclosure provides a method of manufacturing an artificial bone structure for replacement of natural bone, the method comprising:

receiving a three-dimensional (3D) model of the natural bone;

using the 3D model of the natural bone to print a corresponding artificial bone structure using a 3D printer, wherein the artificial bone structure comprises:

a solid cylindrical portion having an elongate shape, wherein the solid cylindrical portion comprises an auxetic structure of a plurality of artificial osteons and wherein each artificial osteon comprises a first hexagonal unit and a second hexagonal unit having corresponding edges, wherein:

the edges of each of the first hexagonal unit and the second hexagonal unit are disposed respectively to form an open end having a predefined gap;

the predefined gap between the edges forming the open end of the first hexagonal unit is equal to the predefined gap between the edges forming the open end of the second hexagonal unit; and the first hexagonal unit and the second hexagonal unit are disposed symmetrically about a central axis by connecting the corresponding edges of the first hexagonal unit and the second hexagonal unit having the gap to form each artificial osteon having a concave shape;

and wherein a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon; and a hollow cylindrical portion having an elongate shape, disposed inside of and concentrically with the solid cylindrical portion, wherein the hollow cylindrical portion is configured to comprise an artificial bone marrow therein.

Figure 1:
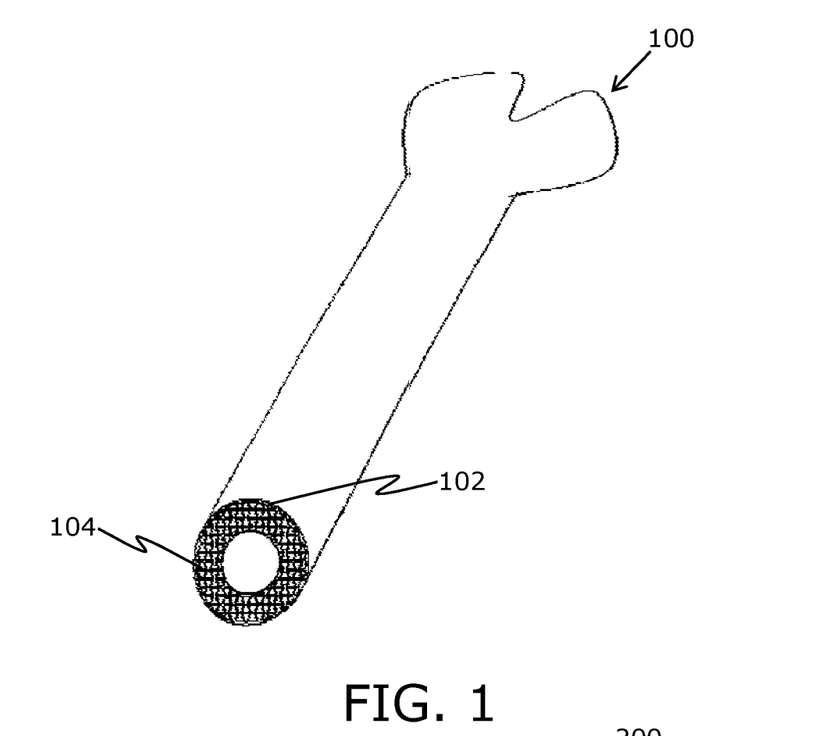
FIG. 1 is a perspective sectional view of an artificial bone structure for replacement of natural bone, in accordance with an embodiment of the present disclosure.

Referring to FIG. 1, there is shown a perspective sectional view of an artificial bone structure 100 for replacement of natural bone, in accordance with an embodiment of the present disclosure. The artificial bone structure 100 can be used as an implant for replacing the natural bone of a person, such as, a natural bone that may have undergone irreparable injury, degeneration with age and so forth. The artificial bone structure 100 can be fabricated to mimic the natural bone of the person, such as, in size and shape thereof.

The artificial bone structure 100 comprises a solid cylindrical portion 102 having an elongate shape. The solid cylindrical portion 102 of the artificial bone structure 100 corresponds to a compact tissue of the natural bone and has an elongate shape that forms a diaphysis (such as a shaft or a central part) of the natural bone. The solid cylindrical portion 102 comprises an auxetic structure of a plurality of artificial osteons 104. Each artificial osteon of the plurality of artificial osteons 104 forms a fundamental unit of the solid cylindrical portion 102. Furthermore, the plurality of artificial osteons 104 forms the auxetic structure, such that the artificial osteons 104 are arranged in a mesh-like configuration. Moreover, the auxetic structure of the plurality of osteons 104 is associated with a negative Poisson's ratio, such that, upon applying force across a single cross-section of the solid cylindrical portion 102 along one direction causes a corresponding increase in thickness of the auxetic structure along a perpendicular direction.

Figure 2:
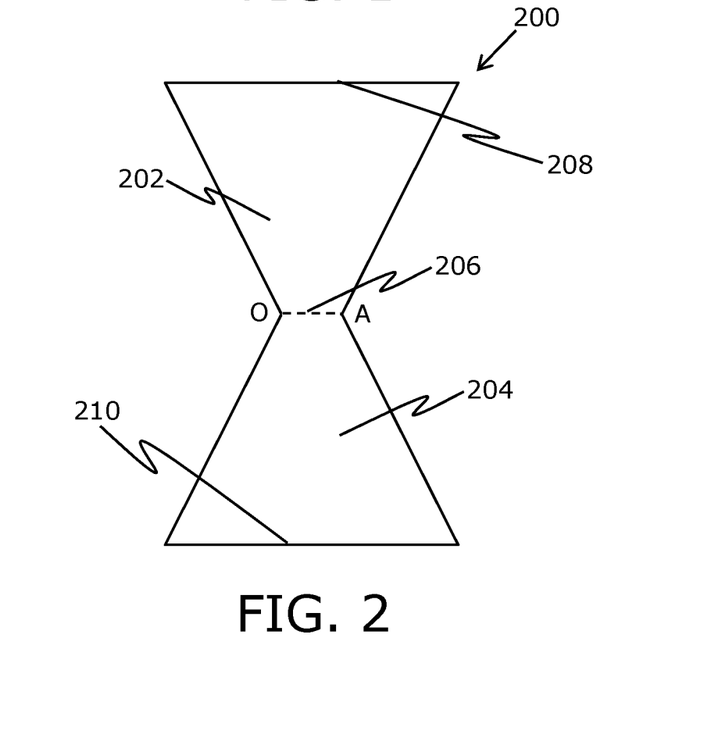
FIG. 2 is a schematic view of an artificial osteon of the plurality of artificial osteons of FIG. 1, in accordance with an embodiment of the present disclosure.

Referring to FIG. 2, there is shown a schematic view of an artificial osteon 200 of the plurality of artificial osteons 104 of FIG. 1, in accordance with an embodiment of the present disclosure. As shown, each artificial osteon 200 comprises a first hexagonal unit 202 and a second hexagonal unit 204 having corresponding edges. Optionally, the first hexagonal unit 202 and the second hexagonal unit 204 are implemented as inverted congruent triangles. The edges of each of the first hexagonal unit 202 and the second hexagonal unit 204 are disposed respectively to form an open end 206 having a predefined gap. It will be appreciated that when the first hexagonal unit 202 and the second hexagonal unit 204 implemented as inverted congruent triangles are disposed together, the open ends 206 of each of the first hexagonal unit 202 and the second hexagonal unit 204 coincide.

Furthermore, the predefined gap between the edges forming the open end of the first hexagonal unit 202 is equal to the predefined gap between the edges forming the open end of the second hexagonal unit 204. For example, when the first hexagonal unit 202 and the second hexagonal unit 204 are implemented as inverted congruent triangles, then the gap formed by the open ends 206 of each the first hexagonal unit 202 and the second hexagonal unit 204 is same. Also, the first hexagonal unit 202 and the second hexagonal unit 204 are disposed symmetrically about a central axis O-A by connecting the corresponding edges of the first hexagonal unit 202 and the second hexagonal unit 204 having the gap 206 to form each artificial osteon 200 having a concave shape. As shown, the artificial osteon 200 is formed to have the concave shape, such that a cross-section thereof corresponds to an hourglass shape or a vertical bow-tie shape.

In an embodiment, each artificial osteon 200 comprises an elongate length between respective top edge of the first hexagonal unit 202 and the second hexagonal unit 204 of each artificial osteon 200 in a range of 5.0 to 6.5 millimeters. For example, a distance between the top edge 208 of the first hexagonal unit 202 and the top edge 210 of the second hexagonal unit 204 is in the range of 5.0 to 6.5 millimeters. Such an edge can be 5.0 millimeters, 5.6 millimeters, 6.2 millimeters, 6.5 millimeters and so forth.

In an embodiment, each artificial osteon 200 comprises the predefined gap 206 of each of the first hexagonal unit 202 and the second hexagonal unit 204 in a range of 0.2 to 1.0 millimeter. For example, the predefined gap the predefined gap 206 of each of the first hexagonal unit 202 and the second hexagonal unit 204 can be 0.2 millimeter, 0.5 millimeter, 0.9 millimeter, 1.0 millimeter and so forth.

In an embodiment, each artificial osteon 200 comprises the edge of each of the first hexagonal unit 302 and the second hexagonal unit 304 having a length in a range of 2.5 to 3.5 millimeters. It will be appreciated that each of the first hexagonal unit 302 and the second hexagonal unit 304 can have three or more edges therein. Consequently, each edge can have a length of 2.5 millimeters, 2.8 millimeters, 3.3 millimeters, 3.5 millimeters and so forth.

In an embodiment, each artificial osteon 200 comprises an angle between adjacent edges of each of the first hexagonal unit 302 and the second hexagonal unit 304 in a range of 60° to 75°. It will be appreciated that adjacent edges of each of the first hexagonal unit 302 and the second hexagonal unit 304 form an acute angle and such an angle can take a value of 60°, 65°, 70°, 75° and so forth.

Figure 3:
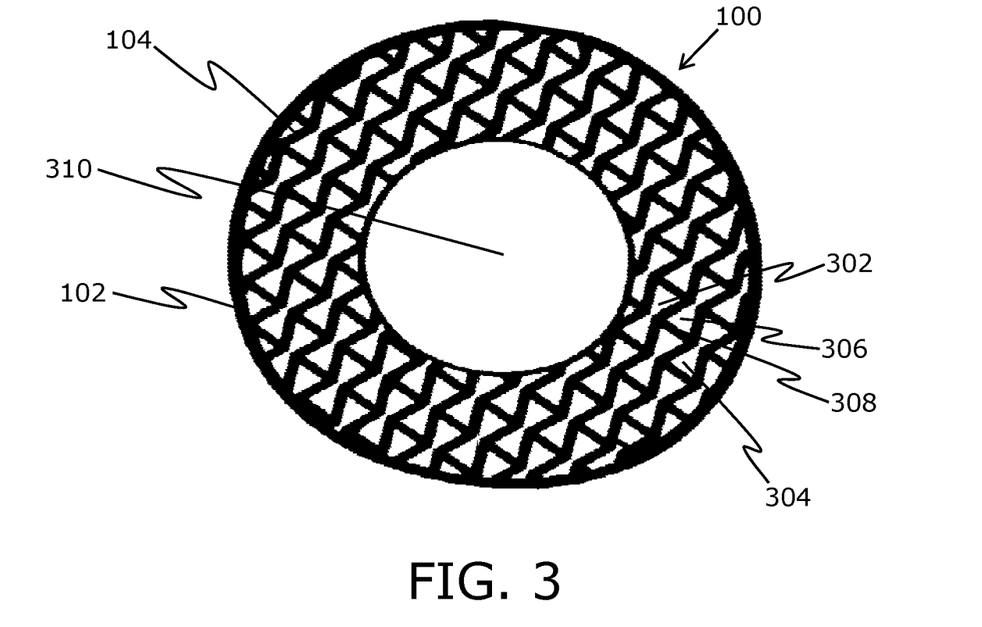
FIG. 3 is a cross-sectional view of the artificial bone structure of FIG. 1, in accordance with an embodiment of the present disclosure.

Referring now to FIG. 3, there is shown a cross-sectional view of the artificial bone structure 100 of FIG. 1, in accordance with an embodiment of the present disclosure. As shown, the plurality of artificial osteons 104 comprises a first artificial osteon 302, a second artificial osteon 304 and a third artificial osteon 306. The first artificial osteon 302 and the second artificial osteon 304 of the plurality of artificial osteons 104 are connected to each other using an edge 308 of the third artificial osteon 306 along an outside of the concave shape of each of the first artificial osteon 302 and the second artificial osteon 304, and about the central axis of each of the first artificial osteon 302 and the second artificial osteon 304. The first artificial osteon 302 and the second artificial osteon 304 of the plurality of artificial osteons 104 are connected by the edge 308 of the third artificial osteon 306 such that the third artificial osteon 306 shares the common edge 308 with each of the first artificial osteon 302 and the second artificial osteon 304. Moreover, the first artificial osteon 302 and the second artificial osteon 304 are connected to each other such that the edge 308 of the third artificial osteon 306 passes along the extrapolated central axes (between edges forming the gap) of each of first artificial osteon 302 and the second artificial osteon 304.

Moreover, the artificial bone structure 100 comprises a hollow cylindrical portion 310 having an elongate shape, disposed inside of and concentrically with the solid cylindrical portion 102. The hollow cylindrical portion 310 is a hollow volume that extends along a length of the solid cylindrical portion 102. The hollow cylindrical portion 310 is configured to comprise an artificial bone marrow (not shown) therein. The artificial bone marrow can be fabricated using a material that can be used to automatically repair the solid cylindrical portion 102 when the solid cylindrical portion 102 suffers damage (for example, a self-healing material), such as, by entering one or more cracks formed within the solid cylindrical portion 102 and subsequently solidifying. In an embodiment, the artificial bone marrow is fabricated using smart polymer.

In an embodiment, the auxetic structure of the plurality of artificial osteons comprises a gap between the first artificial osteon 302 and the third artificial osteon 306 in a range of 0.2 to 1 millimeter. For example, adjacent artificial osteons of the plurality of artificial osteons 104 can be separated by the gap in the range of 0.2 to 1 millimeter, such as, 0.2 millimeter, 0.5 millimeter, 0.9 millimeter, 1 millimeter and so forth.

In an embodiment, the solid cylindrical portion 102 is fabricated using a solution of 80 to 90% by weight of hydroxyapatite and 20 to 10% respectively by weight of Polyacrylonitrile (PAN) or Dimethylformamide (DMF). Such a fabrication of the solid cylindrical portion 102 using the solution of 80 to 90% by weight of hydroxyapatite and 20 to 10% respectively by weight of Polyacrylonitrile (PAN) or Dimethylformamide (DMF) and designed to have the auxetic structure of the plurality of artificial osteons 104 enables the solid cylindrical portion 102 to maintain flexibility thereof. It will be appreciated that hydroxyapatite is a naturally occurring mineral form of calcium apatite and a high concentration thereof in the solution enables rapid regeneration of the solid cylindrical portion 102 when damage is suffered by the solid cylindrical portion 102.

Figure 4:
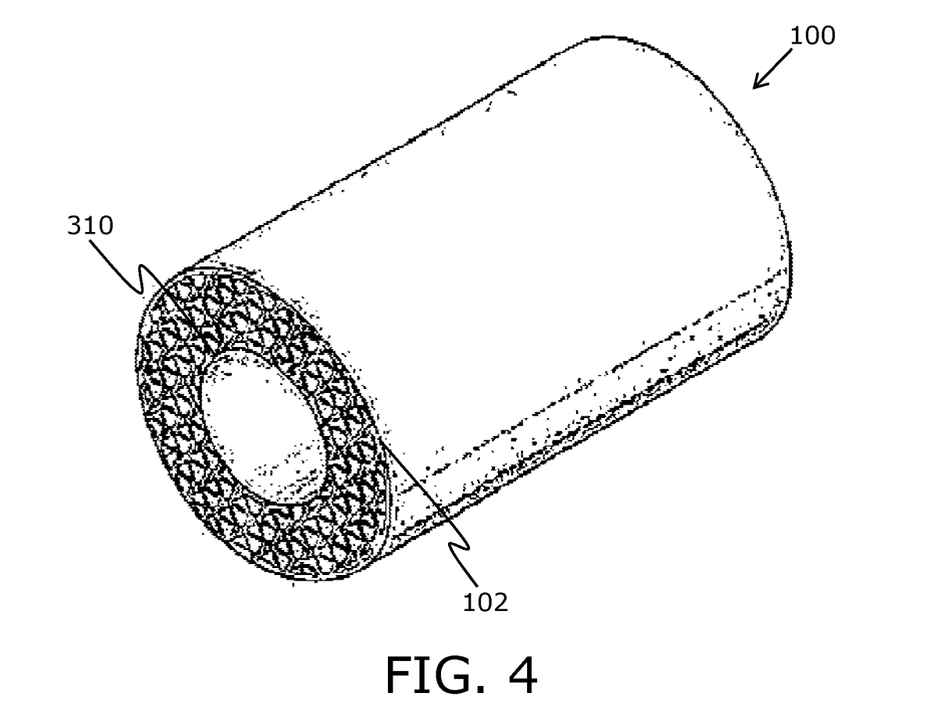
FIG. 4 is a perspective sectional view of diaphysis portion of the artificial bone structure of FIG. 3, in accordance with an embodiment of the present disclosure.

Referring to FIG. 4, there is shown a perspective sectional view of diaphysis portion of the artificial bone structure 100 of FIG. 3, in accordance with an embodiment of the present disclosure. In an embodiment, a diameter of the hollow cylindrical portion 310 is in a range of 20 to 30 millimeters and a diameter of the solid cylindrical portion 102 is in a range of 40 to 50 millimeters. For example, the hollow cylindrical portion 310 can have a diameter of 20 millimeters, 22 millimeters, 25 millimeters, 28 millimeters, 30 millimeters and so forth and the solid cylindrical portion 102 can have a diameter of 40 millimeters, 42 millimeters, 45 millimeters, 48 millimeters, 50 millimeters and so forth.

In an embodiment, a length of the artificial bone structure 100 is in a range of 50 to 70 millimeters. The length of the artificial bone structure 100 that corresponds to a length of the elongate portion thereof (that corresponds to the diaphysis of the natural bone) can have a length of 50 millimeters, 55 millimeters, 60 millimeters, 65 millimeters, 70 millimeters and so forth.

Figure 5:
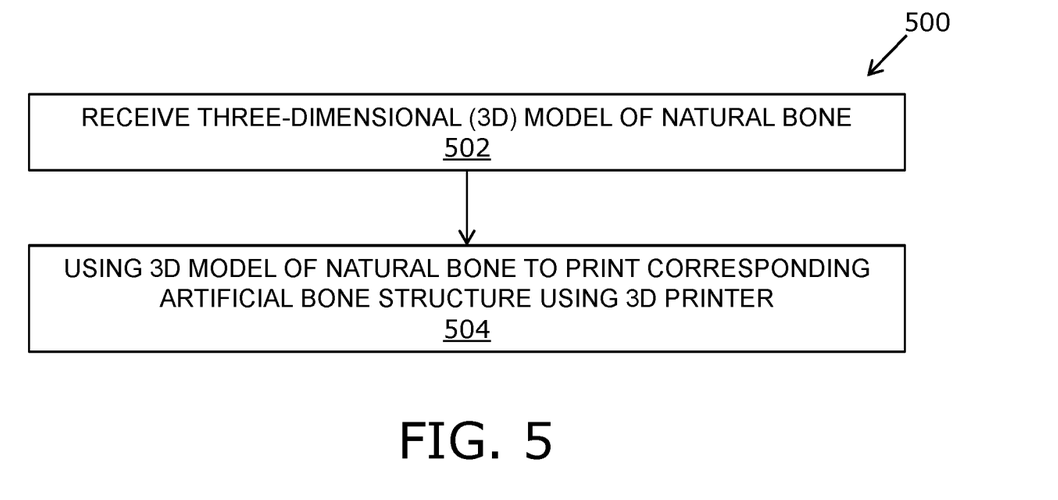
FIG. 5 is a flowchart of a method of manufacturing an artificial bone structure for replacement of natural bone, in accordance with an embodiment of the present disclosure.

Referring to FIG. 5, there is shown a flowchart of a method 500 of manufacturing an artificial bone structure for replacement of natural bone, in accordance with an embodiment of the present disclosure. At a step 502, a three-dimensional (3D) model of the natural bone is received. At a step 504, the 3D model of the natural bone is used to print a corresponding artificial bone structure using a 3D printer. The artificial bone structure comprises a solid cylindrical portion having an elongate shape. The solid cylindrical portion comprises an auxetic structure of a plurality of artificial osteons and each artificial osteon comprises a first hexagonal unit and a second hexagonal unit having corresponding edges. The edges of each of the first hexagonal unit and the second hexagonal unit are disposed respectively to form an open end having a predefined gap. The predefined gap between the edges forming the open end of the first hexagonal unit is equal to the predefined gap between the edges forming the open end of the second hexagonal unit. The first hexagonal unit and the second hexagonal unit are disposed symmetrically about a central axis by connecting the corresponding edges of the first hexagonal unit and the second hexagonal unit having the gap to form each artificial osteon having a concave shape. Furthermore, a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon. Moreover, the artificial bone structure comprises a hollow cylindrical portion having an elongate shape, disposed inside of and concentrically with the solid cylindrical portion, wherein the hollow cylindrical portion is configured to comprise an artificial bone marrow therein.

In an embodiment, a diameter of the hollow cylindrical portion is in a range of 20 to 30 millimeters and a diameter of the solid cylindrical portion is in a range of 40 to 50 millimeters. For example, the hollow cylindrical portion can have a diameter of 20 millimeters, 22 millimeters, 25 millimeters, 28 millimeters, 30 millimeters and so forth and the solid cylindrical portion can have a diameter of 40 millimeters, 42 millimeters, 45 millimeters, 48 millimeters, 50 millimeters and so forth.

In one embodiment, a length of the artificial bone structure is in a range of 50 to 70 millimeters. The length of the artificial bone structure that corresponds to a length of the elongate portion thereof (that corresponds to the diaphysis of the natural bone) can have a length of 50 millimeters, 55 millimeters, 60 millimeters, 65 millimeters, 70 millimeters and so forth.

In an embodiment, the method 500 further comprises preparing at least one filament wire for use in the 3D printer. In one embodiment, each filament wire has a diameter in a range of 1 millimeter to 2 millimeters. For example, each filament wire has the diameter of 1 millimeter, 1.5 millimeters, 2 millimeters and so forth.

In an embodiment, each filament wire is prepared by using a solution of 80 to 90% by weight of hydroxyapatite and 20 to 10% respectively by weight of Polyacrylonitrile (PAN) or Dimethylformamide (DMF). It will be appreciated that when such a filament wire is employed in the 3D printer for 3D printing the artificial bone structure, the resulting artificial bone structure that has been designed to have the auxetic structure of the plurality of artificial osteons enables the solid cylindrical portion thereof to maintain flexibility thereof. It will be appreciated that hydroxyapatite is a naturally occurring mineral form of calcium apatite and a high concentration thereof in the solution enables rapid regeneration of the solid cylindrical portion when damage is suffered by the solid cylindrical portion.

In one embodiment, the method 500 further comprises stirring the solution of hydroxyapatite and PAN or DMF until the solution is homogenized and subsequently, extruding the homogenous solution to obtain the at least one filament wire. In an embodiment, the solution of hydroxyapatite and PAN or DMF is heated using to hot plate to a temperature within a range of 70° C. to 80° C. For example, the solution of hydroxyapatite and PAN or DMF is stirred carefully on a hot plate having a temperature of 75° C. for a period of 30 minutes. Such a heating and stirring process is continued until the solution is mixed well and becomes homogenous. Subsequently, the well-mixed and homogenous solution is used in an extrusion machine to obtain filament wires having a diameter of 2.85 millimeters from the solution.

In an embodiment, the method 500 further comprises receiving a radiographic scan of the natural bone and generating the 3D model of the natural bone using the radiographic scan of the natural bone. For example, the radiographic scan of the natural bone can comprise a 3D X-Ray scan of natural bone of the person or a plurality of CT scans that can be employed to generate the 3D model of the natural bone using respective computer software. The 3D model of the natural bone is further converted to G-codes to be employed by the 3D printer. Subsequently, the 3D model of the natural bone is used in the 3D printer to generate the artificial bone structure corresponding to the natural bone.

The artificial bone structure 100 comprises the auxetic structure of the plurality of artificial osteons to correspond to a structure of a natural bone having a plurality of natural osteons. Furthermore, the auxetic structure of the plurality of artificial osteons enables the artificial bone structure 100 to maintain flexibility similar to the natural bone, such that when the artificial bone structure is used as a medical implant for replacement of natural bone, the artificial bone structure 100 is not easily damaged by its ability to absorb shocks, owing to its elasticity.

The foregoing description of the embodiments has been provided for purposes of illustration and description. Modifications to embodiments of the invention described in the foregoing are possible without departing from the scope of the invention as defined by the accompanying claims. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

I claim:

1. An artificial bone structure for replacement of natural bone, the artificial bone structure comprising:
  a solid cylindrical portion having an elongate shape, wherein the solid cylindrical portion comprises an auxetic structure of a plurality of artificial osteons and wherein each artificial osteon comprises a first hexagonal unit and a second hexagonal unit having corresponding edges, wherein:
  the edges of each of the first hexagonal unit and the second hexagonal unit are disposed respectively to form an open end having a predefined gap;
  the predefined gap between the edges forming the open end of the first hexagonal unit is equal to the predefined gap between the edges forming the open end of the second hexagonal unit; and
  the first hexagonal unit and the second hexagonal unit are disposed symmetrically about a central axis by connecting the corresponding edges of the first hexagonal unit and the second hexagonal unit having the gap to form each artificial osteon having a vertical bow-tie shape;
  wherein the first hexagonal unit and the second hexagonal unit are disposed as inverted congruent triangles such that the predefined gap formed by open ends of each the first hexagonal unit and the second hexagonal unit is same, and wherein the open ends of each of the first hexagonal unit and the second hexagonal unit respectively coincide; wherein the plurality of artificial osteons are arranged in a mesh-like configuration, and associated with a negative Poisson's ratio, such that, upon applying force across a single cross-section of the solid cylindrical portion along one direction causes a corresponding increase in thickness of the auxetic structure along a perpendicular direction; and
  wherein a first artificial osteon and a second artificial osteon of the plurality of artificial osteons are connected to each other using an edge of a third artificial osteon along an outside of the concave shape of each of the first artificial osteon and the second artificial osteon, and about the central axis of each of the first artificial osteon and the second artificial osteon; wherein the first artificial osteon and the second artificial osteon are connected to each other such an edge of the third artificial osteon passes along an extrapolated central axes between edges forming a gap of each of first artificial osteon and the second artificial osteon; and
  a hollow cylindrical portion having an elongate shape, disposed inside of and concentrically with the solid cylindrical portion, wherein the hollow cylindrical portion is configured to comprise an artificial bone marrow therein.

2. The artificial bone structure according to claim 1, wherein each artificial osteon comprises:
  an elongate length between respective top edge of the first hexagonal unit and the second hexagonal unit of each artificial osteon in a range of 5.0 to 6.5 millimeters;
  the predefined gap of each of the first hexagonal unit and the second hexagonal unit in a range of 0.2 to 1.0 millimeter;
  the edge of each of the first hexagonal unit and the second hexagonal unit having a length in a range of 2.5 to 3.5 millimeters; and
  an angle between adjacent edges of each of the first hexagonal unit and the second hexagonal unit in a range of 60° to 75°.

3. The artificial bone structure according to claim 1, wherein the auxetic structure of the plurality of artificial osteons comprises a gap between the first artificial osteon and the third artificial osteon in a range of 0.2 to 1 millimeter.

4. The artificial bone structure according to claim 1, wherein a diameter of the hollow cylindrical portion is in a range of 20 to 30 millimeters and a diameter of the solid cylindrical portion is in a range of 40 to 50 millimeters.

5. The artificial bone structure according to claim 1, wherein a length of the artificial bone structure is in a range of 50 to 70 millimeters.

6. The artificial bone structure according to claim 1, wherein the solid cylindrical portion is fabricated using a solution of 80 to 90% by weight of hydroxyapatite and 20 to 10% respectively by weight of Polyacrylonitrile (PAN) or Dimethylformamide (DMF).

* * * * *